(12) United States Patent
Cattaneo et al.

(10) Patent No.: US 8,500,689 B2
(45) Date of Patent: Aug. 6, 2013

(54) DEVICE FOR CANNULATION OF A HOLLOW ORGAN

(75) Inventors: Giorgio Cattaneo, Tuebingen (DE); Martin Spranger, Entringen (DE)

(73) Assignee: Novalung GmbH, Talheim (DE)

( * ) Notice: Subject to any disclaimer, the term of this patent is extended or adjusted under 35 U.S.C. 154(b) by 0 days.

(21) Appl. No.: 11/897,567

(22) Filed: Aug. 31, 2007
(Under 37 CFR 1.47)

(65) Prior Publication Data
US 2008/0188806 A1    Aug. 7, 2008

(30) Foreign Application Priority Data

Sep. 1, 2006 (DE) .......... 10 2006 042 639
Jul. 24, 2007 (DE) .......... 10 2007 037 050

(51) Int. Cl.
*A61M 29/00* (2006.01)
(52) U.S. Cl.
USPC .......................................................... 604/104
(58) Field of Classification Search
USPC ............... 604/167.03–167.06, 168.01, 65, 604/66, 67, 104–107, 22; 606/301, 304, 606/200, 194, 108, 41, 45, 127, 191, 159, 606/168, 169, 170, 171
See application file for complete search history.

(56) References Cited

U.S. PATENT DOCUMENTS

| | | |
|---|---|---|
| 4,581,017 A | 4/1986 | Sahota |
| 5,224,938 A | 7/1993 | Fenton |
| 5,295,995 A | 3/1994 | Kleiman |
| 5,470,314 A | 11/1995 | Walinsky |
| 5,649,941 A | 7/1997 | Lary |
| 5,746,709 A | 5/1998 | Rom et al. |
| 5,759,172 A | 6/1998 | Weber et al. |
| 6,120,494 A * | 9/2000 | Jonkman ................ 604/506 |
| 6,165,163 A | 12/2000 | Chien et al. |
| 6,270,490 B1 | 8/2001 | Hahnen |
| 6,387,037 B1 | 5/2002 | Bolling et al. |
| 6,390,969 B1 | 5/2002 | Bolling et al. |
| 6,613,038 B2 | 9/2003 | Bonutti et al. |
| 6,673,042 B1 | 1/2004 | Samson et al. |

(Continued)

FOREIGN PATENT DOCUMENTS

| | | |
|---|---|---|
| EP | 0 301 854 | 2/1989 |
| FR | 2 220 283 | 10/1974 |

(Continued)

OTHER PUBLICATIONS

European Search Report for EP 07017119.4, mailed Jan. 14, 2008, 6 pages.

(Continued)

*Primary Examiner* — Nicholas Lucchesi
*Assistant Examiner* — Pritesh Patel
(74) *Attorney, Agent, or Firm* — Seed IP Law Group PLLC (57) ABSTRACT

There is disclosed a device for cannulation of a hollow organ, in particular of an arterial or venous blood vessel of a mammalian body, e.g., human, said device comprising a cannula that has a proximal end, a distal end, and a central section located between the proximal end and distal end. The distal end has an expandable structure which can be converted, for example by means of a dilator, from a non-expanded state to an expanded state, and the expandable structure comprises openings at least in the expanded state.

16 Claims, 3 Drawing Sheets

U.S. PATENT DOCUMENTS

| | | | |
|---|---|---|---|
| 6,679,871 B2 | 1/2004 | Hahnen | |
| 2001/0001812 A1 | 5/2001 | Valley et al. | |
| 2002/0062135 A1* | 5/2002 | Mazzocchi et al. | 606/200 |
| 2002/0188166 A1 | 12/2002 | Viole et al. | |
| 2004/0082906 A1 | 4/2004 | Tallarida et al. | |
| 2005/0027245 A1 | 2/2005 | Sachdeva et al. | |
| 2005/0038408 A1* | 2/2005 | von Segesser | 604/506 |
| 2005/0107820 A1 | 5/2005 | Forsberg et al. | |
| 2006/0036218 A1 | 2/2006 | Goodson et al. | |
| 2006/0167405 A1* | 7/2006 | King et al. | 604/65 |
| 2009/0187133 A1 | 7/2009 | Matheis et al. | |

FOREIGN PATENT DOCUMENTS

| | | |
|---|---|---|
| JP | 61-193670 | 8/1986 |
| JP | 07-504595 | 5/1995 |
| JP | 2001-518325 | 10/2001 |
| WO | WO 94/00178 | 1/1994 |
| WO | WO-2005/002454 | 1/2005 |

OTHER PUBLICATIONS

Office Action from Matheis et al., U.S. Appl. No. 12/416,847, dated Jun. 15, 2010, (13 pages).

Office Action from Matheis et al., U.S. Appl. No. 12/416,847, dated Nov. 29, 2010, (9 pages).

Office Action from Matheis et al., U.S. Appl. No. 12/416,847, dated Jul. 1, 2011, (10 pages).

* cited by examiner

DEVICE FOR CANNULATION OF A HOLLOW ORGAN

CROSS-REFERENCE TO RELATED APPLICATIONS

This application claims priority from German patent application DE 10 2006 042 639.8 filed on Sep. 1, 2006 and German patent application DE 10 2007 037 050.6 filed on Jul. 24, 2007. The contents of the above patent applications are incorporated by reference herein in their entirety.

BACKGROUND OF THE INVENTION

The present invention relates to a device for cannulation of a hollow organ, said device comprising a cannula that has a proximal end, a distal end, and a central section located between the proximal end and distal end, and the cannula, after introduction into the vessel, is in fluid communication with the vessel.

Devices of this kind that comprise a cannula are used in a variety of ways in the surgical and medical field, for example for cannulation of arterial or venous blood vessels. A typical cannula is a small tube which in most cases has a fixed diameter and which a surgeon or physician uses in order to withdraw blood or in order to create a passage for blood between a patients' circulation and an extracorporeal system. Thus, an extracorporeal circuit, for example for extracorporeal blood oxygenation, can be maintained by a blood pump, or, if the endogenous blood pressure is used, without a pump. Extracorporeal lung assist (iLA, AVCO2R, pECLA, ECMO, etc.) is used in patients with acute lung failure in whom, while avoiding the risks of conventional ventilation, carbon dioxide is removed from the blood and oxygen enrichment takes place. The oxygen-rich blood is then returned to the patient. To do this, two individual cannulas or a double-lumen cannula are introduced into peripheral vessels, after which the blood flows via a short hose system through what is called a membrane lung and then back into the patient's circulation. In intensive care medicine, cannulas are inserted, for example, through a peripheral vessel of the leg or neck. This system has the advantage that a sufficient gas exchange can be achieved over a period of days or even weeks, as a result of which it is possible to avoid aggressive forms of ventilation, for example, and ventilator-associated lung injury (VALI), and the lung is able to regenerate.

Cannulas of different dimensions and diameters can be used depending on the vessel, in particular depending on the latter's size. Flexible catheters or cannulas usually have a fixed lumen and a fixed size in terms of their external diameter. In a heart-lung bypass, for example, a large lumen has to be provided in order to permit a sufficient flow of oxygenated blood. For this purpose, a traditional catheter or a cannula must have a large diameter, which in turn makes it difficult to insert the cannula/catheter into the vessel, in particular to pass it through tissue, and can lead to a surgical intervention that entails greater damage to the surrounding tissue.

In cannulation of arterial vessels with small cannulas, the smaller diameter of the lumen means that the resistance of the blood flow inside the cannula increases, which has the result of limiting the flow rate. High flow rates are enforced when blood pumps are used, and the resulting high shearing stresses in the blood stream represent a danger of damage to blood cells.

Larger cannulas, on the other hand, permit higher flow rates with at the same time less stress on the blood. However, the danger of using larger cannulas is that the blood vessel is closed after introduction of the cannula, and the physiological flow conditions in other areas of the circulation are disturbed. For example, when access is made into an arterial vessel, the physiological flow of blood in the downstream blood circulation, for example in the extremities or in other organs, may be prevented. This blocking of the flow of blood there can lead to ischaemia, an imbalance between oxygen and nutrient demand and supply, with consequent necrosis of the affected tissue. Moreover, cannulation of a venous vessel can cause congestion of the flow of blood back to the heart, with resulting organ damage and the danger of coagulation.

Because of the dangers outlined above, it is therefore important to determine the size of the cannula in a pumpless extracorporeal circuit with arterio-venous connection, and similarly in a veno-venous or veno-arterial extracorporeal circuit with blood pump. As has been mentioned above, the flow rate of the blood in the absence of a pump is dependent on the physiological blood pressure conditions in the circulation, on the size of the cannula, and on the resistance of the extracorporeal system (artificial lung, haemofilter, hoses, etc.).

To achieve higher flow rates of blood, cannulas with a large lumen are required, but this may again entail the abovementioned disadvantage of ischaemia or venous blood congestion.

Since the blood pressure in the venous circulation is low, pressure has to be built up to permit active venous drainage for the extracorporeal circuit, and this is achieved by using a pump. At high flow rates of blood through the cannula, the blood pressure may drop, thus leading to an underpressure in the vessel. This can lead to collapse of the vessel, since the vessel walls are pressed inward by the pressure prevailing outside the vessel, which leads to occlusion of the vessel and to interruption of the blood flow.

Therefore, the diameter and the length of the venous cannula, as a function of the desired flow of blood, are also important considerations in the case of venous blood supply into an extracorporeal circuit with veno-venous or veno-arterial connection. For example, it also determines the extent or the avoidance of blood trauma caused by underpressure and resulting excessive shearing forces.

The prior art discloses cannulas whose lumen can be widened along their entire length, and cannulas which additionally have an occlusion balloon at one end.

Thus, U.S. Pat. No. 6,613,038 B2 discloses a cannula which is inserted through the tissue in a non-expanded state with a small diameter, and which, after removal of a cannula sleeve, then expands radially outwards along its entire length as soon as it has been inserted into the desired vessel or tissue.

Moreover, U.S. Pat. No. 6,679,871 discloses a cannula which, along the length of its lumen, has an inflatable balloon that can be expanded after introduction into a blood vessel. This catheter can further comprise an occlusion balloon which, after its expansion, completely closes the vessel.

However, the abovementioned embodiments of cannulas are not able to overcome the problems known in the prior art, since with these cannulas too there is a danger of the vessel becoming occluded and, in an arterial application, of the flow of blood in the extremities being prevented.

SUMMARY OF THE INVENTION

It is an object of the present invention to make available a device for cannulation of a hollow organ, which device is able to overcome the disadvantages described in the prior art.

According to one aspect of the invention, there is provided a device for cannulation of a hollow organ of an mammalian body, said device comprising a cannula that has a proximal end, a distal end, and a central section located between the proximal end and distal end, and the cannula, after introduction into the vessel, is in fluid communication with the vessel, whereby the distal end has an expandable structure which can be converted from a non-expanded state to an expanded state, and the expandable structure comprises openings at least in the expanded state.

The mammalian body can be human or animal.

In this document, the term "proximal" designates the end of the cannula which is directed towards the user and which comes to lie outside the vessel after insertion of the cannula.

The term "distal" designates that end of the cannula pointing away from the user and intended to be inserted into the vessel.

The device according to the invention ensures on the one hand, after insertion of the cannula into a vessel, the creation of the passage of blood between the blood circulation and the extracorporeal system, and, on the other hand, the openings in the expandable structure ensure that the areas of a patient's body situated downstream from the cannulation site continue to be supplied with blood. Ischaemia and tissue necrosis are thus advantageously avoided.

Moreover, in the cannulation of a venous vessel, particularly a peripheral vessel such as the femoral vein or jugular vein, the openings in the expandable structure at the distal end ensure that the vessel lumen is kept patent, and collapse of the vessel is avoided. At the same time, suctioning of the vessel wall by the cannula is avoided, and also the resulting closure of the cannula, such that in this way the flow of blood in the vessel and also the flow of blood in the venous cannula are secured. Moreover, there is no danger of haemolysis and of associated erythrocyte damage and leukocyte activation, which can be caused by suction effects.

The stated advantages are—inter alia—achieved by the fact that, after introduction of the cannula into the vessel, the distal end can be expanded, while at the same time the openings of the expanding structure of the distal end are opened. With the expansion, the expanding structure of the distal end can additionally position itself, for example, onto the vessel wall of the blood vessel, thus also advantageously ensuring a secure fit of the cannula in the vessel. Regardless of whether the expandable structure lies on the vessel wall or not, the expandable structure generally ensures that, between cannula and vessel wall, a space is obtained that prevents occlusion of the vessel.

To ensure sufficient withdrawal of blood, the cannula is additionally of such a size and diameter that it does not lie completely on the vessel walls, and instead, in its area extending from the proximal end and via the central section, it has a greater diameter than the vessel. The distal end preferably has a smaller diameter than the proximal end and the central section before and during the insertion of the cannula, in order to permit the gentlest possible access to the vessel.

The expandable structure and the openings provided therein ensure that some of the blood is able to flow past the cannula and thus reaches areas of the body located downstream of the cannulation site, resulting in a sufficient supply of blood to these vessels and in particular to the extremities. On the other hand, it is possible to ensure that a sufficient amount of blood can be withdrawn from the body via the cannula. The blood withdrawn from the vessel via the cannula is delivered, for example, to an extracorporeal circuit and, in the case of an extracorporeal heart-lung circuit, is enriched with oxygen, for example via membrane oxygenators, and then returned to the body via venous or arterial cannulas. It is also ensured that, in venous cannulation, the vessel does not collapse at or near the cannulation site, and, in this way, a venous underpressure and consequent blood damage are avoided.

With the cannula according to the invention, a device for cannulation of an arterial or venous blood vessel is made available which permits a small resistance to the blood flow and at the same time permits a physiological return flow from the periphery of the body. With the present invention, it is possible to avoid the cannula leading to occlusion of the vessel and thus impairing the flow of blood around the cannula.

A further advantage of the device according to the invention is that the cannula can be adapted in terms of its size and its average diameter to the respective vessel that is to be cannulated, thereby permitting an increased flow of blood inside the cannula despite the restricted size at the time of insertion. It will be clear to the specialist that the size and the diameter of the cannula depend on the size of the vessel that is to be cannulated and can accordingly vary as a function of the patient, the desired application purpose and the vessel.

During the insertion through the vessel wall, the expandable structure at the distal end of the device is maintained in a compressed/cross-section-compressed or non-expanded state and has a restricted diameter. After introduction of the cannula into the vessel, the distal end with the expandable structure can be converted to the expanded state, as a result of which the expandable structure at the distal end can come into contact with the vessel wall. By means of the radially directed force exerted by the expandable structure, the vessel is kept open, in particular by a space being ensured between the cannula and the vessel walls.

According to the invention, the expanded tip has openings that allow some of the blood to flow past. The proportion of the blood that does not flow through the cannula and then out of the body can therefore advantageously flow around the cannula with slight flow resistance.

In a refinement, the expandable structure is a self-expandable structure.

In this case, the device in the so-called rest state, i.e., the expanded state, has an already expanded structure at its distal end, such that by exerting a force on the expanded structure, the latter can be converted to a compressed state. In this compressed state, the device can be inserted into the desired vessel, and, after positioning in the vessel, the force ceases and the structure converts back to the expanded state. This conversion to the expanded form is referred to in comparable specialist fields as self-expandable.

In this refinement, the cannula, in particular the tip or distal end of the cannula, can be produced already in the expanded configuration, which thus corresponds to its rest state. Before and during the insertion into the vessel, the distal end with the expandable structure can be subjected to a force or pressure in such a way that the expandable structure is extended by means of the compression into an elongate shape, as a result of which the distal end narrows in comparison to the rest of the diameter of the cannula. When the pressure or force is removed following insertion into the vessel, the expandable structure of the distal end returns to its original expanded configuration. If the cannula is to be removed again after use, the expandable structure of the distal end is once again converted by force into the compressed state extending in the longitudinal direction with respect to the cannula, as a result of which the tip or distal end again narrows and can be easily removed from the vessel.

In another embodiment, the expandable structure can be converted into the expandable state by the action of a force or pressure, for example. This can be done, for example, by an inflatable balloon that is provided inside the expandable structure. The widening balloon transmits the force to the expandable structure, as a result of which the latter is converted to the expanded state.

In a further refinement, the expandable structure has a material chosen from the group comprising elastic plastics, superelastic plastics, elastic metals, superelastic metals, in particular nitinol.

In another embodiment, the expandable structure has a material with shape-memory properties.

From a number of materials known in the prior art, it will be evident to the specialist which material can or has to be chosen, with the prior art designating nitinol in particular as a suitable material.

In another embodiment, the expandable structure has the configuration of a self-expandable braided stent.

Self-expandable braided stents are sufficiently known and described in the prior art. They comprise wires that have been braided at a certain angle and that deploy automatically when a compressive sheath is removed.

The openings in the expandable structure can be configured depending on the specific angle at which the stent is braided. According to the preferred example, this structure can be located at the distal cannula end of the device according to the invention and then forms the expandable structure.

In another embodiment of the device according to the invention, the cannula has a wire-reinforced, stent-like main frame, the proximal end and the central section being coated with a plastic in order to form a liquid-tight tube section.

In this embodiment, the wire structure gives the cannula stability along its length, while at the same time the distal end is free from the elastic plastic and therefore has openings whose size and shape are predetermined by the braiding angle of the wire-reinforced main frame. Furthermore, the distal end, not coated with a plastic that confers stability, is able to expand after the pressure is removed, as a result of which the openings are freed.

In another embodiment, the angle at which the wire of the main frame is braided is variable along the length of the latter.

By means of this measure, it is possible, in different areas of the main frame, and also of the cannula, to achieve a different angle, in order in turn to regulate the size of the openings.

In another preferred embodiment, the plastic with which the device according to the invention can be at least partially coated is chosen from the group comprising polyurethane, silicone and Teflon.

Accordingly, in this illustrative embodiment, a braided wire stent is first of all produced, for example, which has a very specific braid angle either along its entire length or only in certain sections. This "main frame" is then coated with a plastic at its proximal end and in its central section, whereas the distal end remains free of the plastic coating. The proximal end and the central section thus form a leaktight tube through which blood can be passed, for example, whereas the distal end is uncoated and has the structure of a braided stent. At the distal end, in the expanded state, the latter thus forms openings that are formed by the angle of the intersecting/overlapping wires of the braided stent. With the expanded end, the cannula can be anchored in the vessel, by means of the wires settling on the vessel wall. Moreover, blood can flow past the cannula via the openings, and not just into the cannula, and this means, in the case of an arterial cannulation, that the areas of the patient's body located downstream are supplied with blood, and, in the case of a venous cannulation, the physiological flow back to the heart is guaranteed, and congestion or thrombosis of venous blood is avoided.

In another embodiment, the device moreover comprises a dilator with a proximal area and a distal area and with a central section located between the proximal area and distal area, which dilator is used to insert the cannula and is provided inside the latter.

A dilator is a customary component part of cannula devices. With a dilator, the vessels are expanded and thus prepared for the insertion and placement of the cannula in the vessel. In the device according to the invention, the dilator is thus inserted into the cannula in order to make it easier to insert the cannula into a vessel, and it thus forms an integral part of the device.

In one embodiment of the device according to the invention, the expandable structure can be displaced along its length through the dilator.

In this embodiment, the dilator, which in any case is often a component part of a cannulation system, can be used for inserting the cannula in its non-expanded state. Prior to the insertion of the cannula into the vessel, the dilator is inserted into the cannula and wedges itself on the distal end of the cannula with the expandable structure such that, upon further advancement of the dilator into the cannula, the expandable structure is displaced or stretched lengthwise. By means of this displacement, the original diameter of the expandable structure is reduced.

In a refinement, the expandable structure is converted to its expanded state through removal of a dilator that is guided inside the device for insertion of the cannula into a vessel.

The dilator is guided inside the cannula for the purpose of inserting the device and, upon passage through the skin and through the vessel wall, ensures the stability of the cannula and serves to expand the vessel. The dilator is able to exert the force needed to convert the expandable structure of the distal end to the non-expanded state or the elongated shape.

This can be achieved, for example, by a particular design of the distal area of the dilator according to which the dilator, on its outer surface in this area, has structures which wedge with the expanding structure upon insertion of the dilator into the cannula and, upon further advancement in the distal direction, stretch the expandable structure lengthwise. Upon withdrawal of the dilator, the expandable structure disengages itself from the structures of the surface of the dilator, as a result of which the latter can be guided through the cannula and out of the vessel, and the expandable structure of the distal end of the cannula is converted to its expanded state.

This measure can be achieved, for example, by the expandable structure at the distal end of the device having the form of a spherical wire-reinforced main frame attached to the central section. The end of this main frame opening towards the vessel is narrowed and has a smaller diameter than a distal area of the dilator. Using an elastic material, preferably a superelastic material, for the expandable structure, i.e., the main frame, together with the smaller diameter of the main frame, means that when the dilator is inserted into the cannula it entrains the narrowed structure along with it in the direction of sliding, as a result of which the expandable structure is stretched lengthwise. The extent by which the expandable structure is stretched lengthwise depends on the material used for the expandable structure and, where appropriate, on the braid angle, if a braided main frame is used.

On the other hand, however, in another refinement, a flexible sleeve or a sleeve-like section is provided which, in order to insert the device into a vessel, is guided at least over the expandable structure and thus maintains the expandable structure in the non-expanded state before and during insertion of the device. After correct positioning of the cannula, the sleeve can then be removed, for example by being pulled back in the direction of the user, as a result of which the expandable structure is released and is able to expand.

A further feature of the devices according to the invention is the variable lumen of the cannulas. For introduction of the cannula, the cannula tip, that is to say the distal end located in the vessel, has a smaller diameter than the proximal part and/or central section of the cannula. This reduces the risk of injury and disturbance of the flow conditions outside the cannula. In contrast to the cannulas known in the prior art, it is therefore not necessary to push the cannula deep into the vessel in order to secure the position of the cannula also by a relatively wide diameter. With the expandable structure, it is possible to ensure at least a space between the vessel walls and the cannula. The cannula can thus be inserted with only a small part of its distal end into the vessel, the distal end having a smaller diameter upon insertion into the vessel, thereby avoiding risk of injury to the vessel. At the same time, the cannula has a greater diameter in the part lying outside the vessel, i.e., at the proximal end, as a result of which the overall resistance to the flow of blood in the cannula decreases. The increase in diameter no longer poses any risk of injury now, because the tissue outside the vessel can be stretched without any adverse consequences.

Further, the thin part of the cannula, that is to say the distal end, located inside the vessel is considerably shorter than the wider part outside the vessel, thereby ensuring a very small overall resistance.

The cannula can be inserted to the desired length into the vessel in different ways.

In another embodiment, the dilator has a channel-like passage that extends from the distal area of the dilator to at least the central section of the dilator.

The passage can be provided either as a channel-like depression on the outer surface of the dilator, or as a channel provided completely within the dilator.

In a refinement of this embodiment, the channel-like passage is provided as an elongate depression on the surface of the dilator, with one end of the passage being provided as an inlet in the distal area of the dilator, and the other end of the passage being provided as an outlet in the proximal end or in the central section.

With this embodiment, the vessel side can be directed to the user side via the channel-like passage. This means that when the cannula is pushed with the dilator into the vessel, and when the distal end of the cannula and also of the dilator is located inside the vessel, the prevailing capillary forces and the blood pressure cause the blood located in the vessel to flow into the channel-like depression. By way of the channel-like depression, which has its start, i.e., the inlet, at the distal end, the blood is then guided at least as far as the central section of the dilator, where it becomes visible to the user as it emerges from the outlet of the channel-like passage. The user can therefore see that the positioning of the device was successful, and that the cannula can be deployed in a next step by removing the dilator.

In another embodiment, the inlet and the outlet of the channel-like passage are each provided with a membrane-like cover. In a refinement of this embodiment, the channel-like passage of the dilator contains a free-flowing or gaseous medium, for example air, nitrogen, saline solution.

This measure has the advantage that it is also possible to establish the success of the vascular access without blood passing through the passage of the dilator.

In the embodiment with the membrane-like cover, when the cannula is located in the vessel, the membrane across the inlet of the channel-like passage is stretched by the blood pressure in the vessel and is pressed inward. If a further membrane seals off the passage at the other end of the channel-like passage, or at the outlet, this latter membrane bulges out on account of the increased pressure in the passage.

In a further embodiment, provision can be made for the passage to contain gas, which is preferably compressible.

It is also possible for a liquid to be present in the passage, such that, when successful vascular access has been achieved, the membrane at the user side bulges outward under the effect of the volume displacement of the liquid in the passage. In this case, the liquid can be a saline solution, for example, which is either already present in the dilator or is introduced by the user before use.

In another embodiment, the membrane of the dilator at the vessel side has a substantially greater surface area than the membrane at the user side.

In this refinement, a small bulging of the membrane-type cover at the blood side leads to a greater bulging at the user side, and thus provides a clear signal to the user.

In a refinement, at least some parts of the device according to the invention are coated with at least one biocompatible material. Such a material is chosen in order to reduce, if not completely eliminate, the risk of blood coagulation and of inflammatory reactions triggered by the vessels and blood coming into contact with foreign material. Various natural and/or synthetic materials suitable for the claimed use are known to the specialist from the prior art.

In another embodiment, the cannula has a variable diameter along its length.

With this refinement, for example, the distal end of the cannula for inserting the cannula into a vessel can have a smaller diameter than the proximal end or the central section of the cannula. Correspondingly, the dilator to be introduced into the cannula can be adapted to the shape and thus to the different diameters of a cannula.

The present invention further relates to the use of the device in an extracorporeal circulatory system.

In such methods, the device according to the invention can be employed, for example, in connection with a lung-assist device in extracorporeal lung assistance. The novel device ensures the supply of blood to areas situated downstream of the cannulation site.

With the present invention, a device for cannulation of a blood vessel is made available with which, by means of the narrow and expandable cannula tip, a rapid and gentle vascular access is permitted under variable anatomical and physiological conditions, even in emergency applications. The device according to the invention substantially reduces the risk of injury and of overextension posed by large cannulas. It further avoids occlusion of the peripheral vessel by the cannula through expansion of the distal end, such that the extremities of the body can also be perfused with blood at physiological blood flow rates. Moreover, the rate of flow inside the cannula is maximized under physiological conditions. The flow resistance within the small cannula diameter inside the vessel is compensated by the low resistance in the large diameter outside the cannula. Overall, the resulting cannula resistance is therefore lower than in traditional cannulas, but the flow of blood to the extremities and the return flow of venous blood from the extremities to the heart is not impaired.

Further advantages will become evident from the attached drawings and from the following description.

It will be appreciated that the aforementioned features and those still to be explained below can be used not only in the respectively given combination, but also in other combinations or on their own, without departing from the scope of the present invention.

BRIEF DESCRIPTION OF THE DRAWINGS

Exemplary embodiments of the invention will be explained in more detail in the following description and are depicted in the drawing. In the drawing.

DESCRIPTION OF PREFERRED EMBODIMENTS

Figure 1:
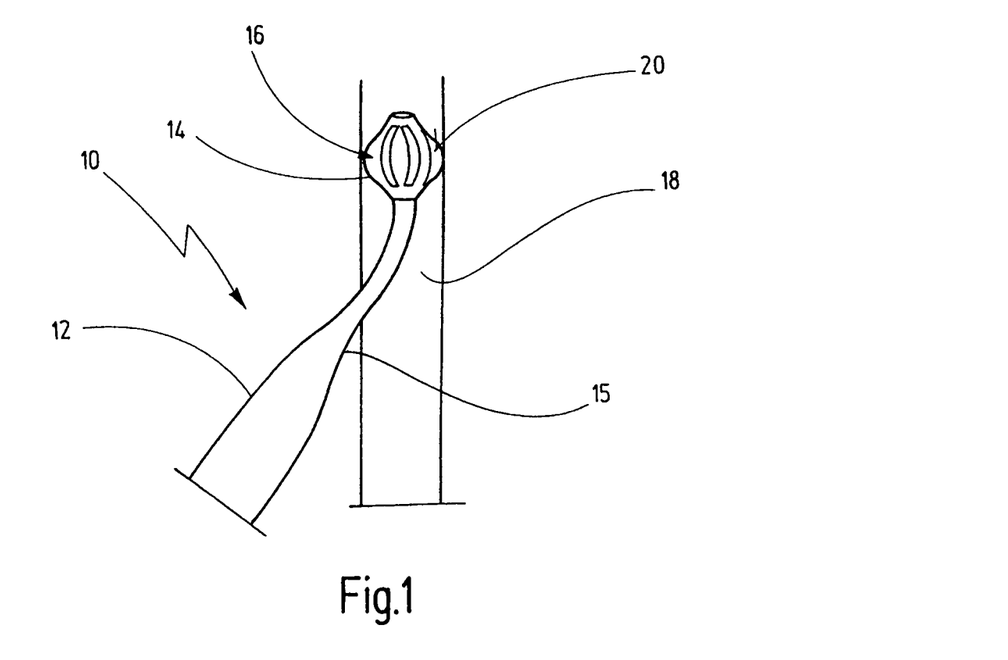
FIG. 1 shows a detail of an embodiment of the device according to the invention, in which detail the distal end with the expandable structure can be seen.

In FIG. 1, a detail of an embodiment of the device according to the invention for cannulation of a blood vessel is designated generally by reference number 10. The device 10 comprises a cannula 12 with a proximal end, a distal end 14, and a central section 15 located between the proximal end and the distal end 14. The distal end 14 has an expandable structure 16, which lies in the expanded state in the vessel 18. Moreover, reference number 20 designates openings in the expandable structure 16. The cannula 12 also comprises a cannula opening through which the fluid communication of the vessel with the device is established.

As can be seen from FIG. 1, the distal end 14 of the cannula 12 has been inserted into the vessel 18. In FIG. 1, the expandable structure 16 of the distal end 14 has positioned itself in the expanded state onto the vessel walls. However, the expandable structure does not necessarily have to position itself onto the vessel walls, since its shape alone ensures that the cannula is spaced apart from the vessel walls. In this way, it secures the fit of the cannula 12 and of the device 10 as a whole in the vessel. After the device has been inserted into the vessel 18, some of the blood carried in the vessel 18 thus passes through the cannula opening into the cannula 12 and then passes outside a patient's body, for example into an extracorporeal circuit, such as an extracorporeal lung assist device. The rest of the blood, not guided into the cannula 12, flows past the cannula via the openings 20 and reaches vessel areas below the cannulation site. This ensures the supply of blood to these vessel areas, not least to the extremities.

The openings in the expandable structure can have any desired shape, especially ones that are suitable from the point of view of flow technology, in other words shapes that permit a favorable ratio of distribution between the blood to be discharged through the cannula 12 and the blood to be conveyed onwards in the vessel 18.

Figure 2A:
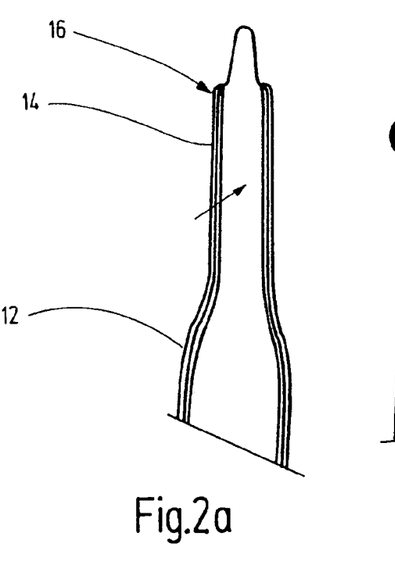
FIG. 2a shows a detail of an embodiment of the device according to the invention, namely the distal end in cross section, with the expandable structure in the state when subjected to a force.
Figure 2B:
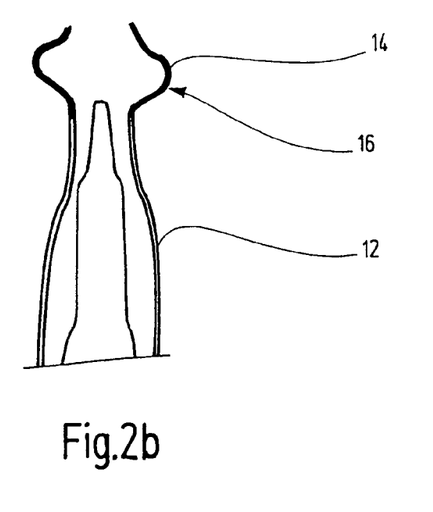
FIG. 2b shows the detail from FIG. 2a, the expandable structure being in the expanded state here, since the force has been removed.

FIGS. 2a and 2b show details once again of an embodiment of the device according to the invention, where the same elements as in FIG. 1 have been provided with the same reference numbers. In FIGS. 2a and 2b, the distal end 14 of the cannula 12 is shown in longitudinal section together with the expandable structure 16, and with a dilator 22 also present in the cannula 12.

The dilator can be a standard dilator used in this field and can be made of materials such as plastics. As has already been mentioned above, dilators are generally used to expand the vessels into which the cannulas are to be introduced.

In FIG. 2a, the expandable structure is in its non-expanded state. Moreover, the dilator 22 is guided through the cannula 12 and also extends through the expandable structure 16 and thus stretches or displaces the latter along the longitudinal axis of the dilator, thereby reducing the cross section that the expandable structure has in the expanded state. The displacement can be achieved, for example, by a wedging of the dilator with the expandable structure. In this state, the expandable structure 16 is accordingly subjected to a force with which it is held until the cannula 12 has been successfully positioned in the vessel 18.

FIG. 2b shows the expanded state of the expandable structure 16 of the distal end 14 of the cannula 12, into which state it is converted after the cannula 12 has been positioned in the vessel 18. It reaches this state through removal of the dilator 22 and through the resulting cessation of the force. In this illustrative embodiment, the expandable structure has or is made of a material with superelastic properties, which means that the expandable structure can be produced in the expanded form, can be compressed for insertion into a vessel, and can recover its original shape after the cannula 12 has been positioned in the vessel 18 and after the force acting on it has been removed.

Figure 3:
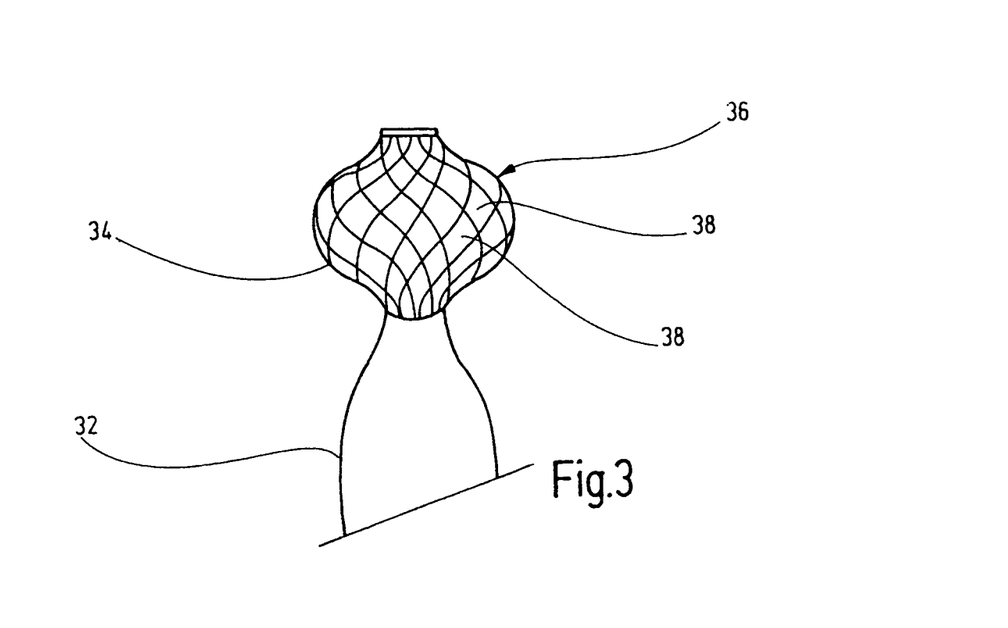
FIG. 3 shows a detail of another embodiment of the device according to the invention.

FIG. 3 shows a detail of another embodiment of the device according to the invention, where the distal end 34 of the cannula 32 has an expandable structure 36. As can be seen from FIG. 3, the expandable structure 36 has the form of a braided wire structure in the manner of a braided stent. The embodiment shown in FIG. 3 is in the expanded state. As can be seen from FIG. 3, the expandable structure 36 has openings 38 which, once the cannula 32 has been positioned in a vessel, ensure that some of the blood carried in the vessel is guided past the cannula into areas located below the cannulation site, in particular to the extremities.

According to the invention, the main frame of the device can have a braided wire structure whose proximal end and central section are coated with a plastic. Coating these sections results in the creation of a liquid-tight, tubular cannula section which, at its distal end, still has the configuration and shape of the braided structure. The main frame can have different braid angles along its length.

The device can also be designed in such a way that the expandable structure is produced separately and is connected fixedly to the other sections of the cannula.

Figure 4A:
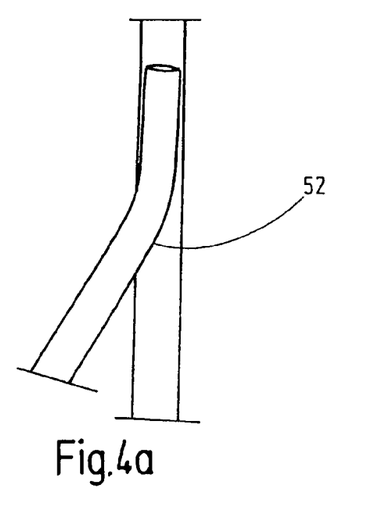
FIG. 4a shows a cannulation procedure from the prior art.
Figure 4B:
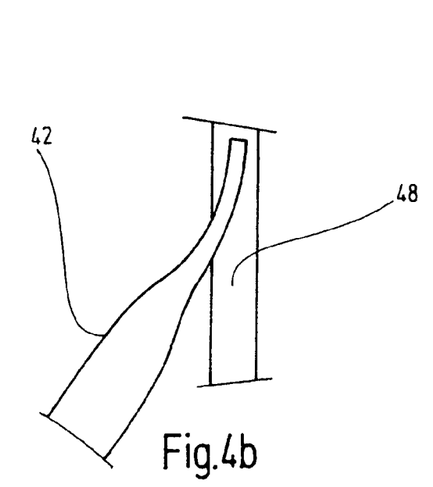
FIG. 4b shows an embodiment of the device according to the invention being introduced into a blood vessel.

FIGS. 4a and 4b illustrate a principle difference between cannulas of the prior art and embodiments of the device according to the invention. The cannulas 52 known in the prior art, shown in FIG. 4a, have a constant diameter, whereas the device according to the invention, shown schematically in FIG. 4b, can have a variable lumen. The cannula 42 has a smaller diameter inside the vessel 48, thus reducing the risk of injury and the risk of disrupting the flow conditions outside the cannula. At the same time, the cannula outside the vessel 48 has a greater diameter than the section of the cannula located within the vessel, thereby decreasing the overall resistance to the flow of blood in the cannula. Since the thin part of the cannula 42 inside the vessel 48 is considerably shorter than the part of greater diameter outside the vessel 48, there is a very low resistance overall. The possibility of keeping the part of the cannula located inside the vessel 48 short is afforded by the expandable structure, not shown in FIG. 4b. In this embodiment of the device according to the invention, it is this structure that allows the cannula to be anchored in a vessel, with the result that it is not necessary to insert longer sections into the vessels in order to achieve secure positioning.

Figure 5:
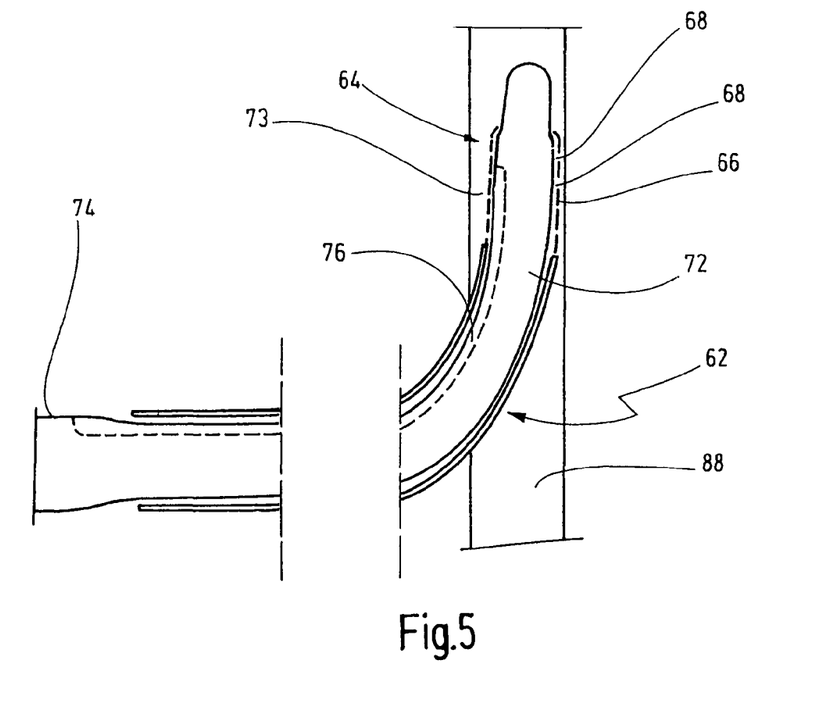
FIG. 5 shows an embodiment of the device according to the invention, in which the dilator has a passage.

FIG. 5 shows a detail of another embodiment of the device according to the invention. In FIG. 5, reference number 62 designates the cannula as a whole, and reference number 64 designates the distal end of the cannula 62. The expandable structure is indicated by reference number 66, and the openings of the expandable structure 66 are designated by reference number 68. It will also be seen from FIG. 5 that that the cannula 62 has been inserted into a vessel 88 with the aid of a dilator 72. The dilator 72 has a passage 76, which is indicated by broken lines in FIG. 5. The passage 76 is located on a top face of the dilator 72 and, starting from the distal section 73 of the dilator 72, extends at least into a central section 74 of the dilator 72. By introducing the dilator 72 into the cannula 62, and thus also into the expandable structure 66, the latter is displaced in the longitudinal direction of the dilator 72. Blood flows into the passage 76 by way of the openings 68 provided in the expandable structure 66. Since the central section of the cannula 62 has no openings, the cannula seals off the passage 76 in the further longitudinal continuation thereof, such that the blood flowing through the openings 68 into the passage 76 is guided through the passage 76 up to the latter's outlet, which is located in the central section or at the proximal end of the dilator 72, at any rate in the area of the dilator 72 no longer located inside the cannula. Therefore, as soon as blood emerges from the outlet of the passage 76 after the cannula 62 has been introduced into a vessel, the person using the device can tell that the cannula has been introduced far enough.

Figure 6A:
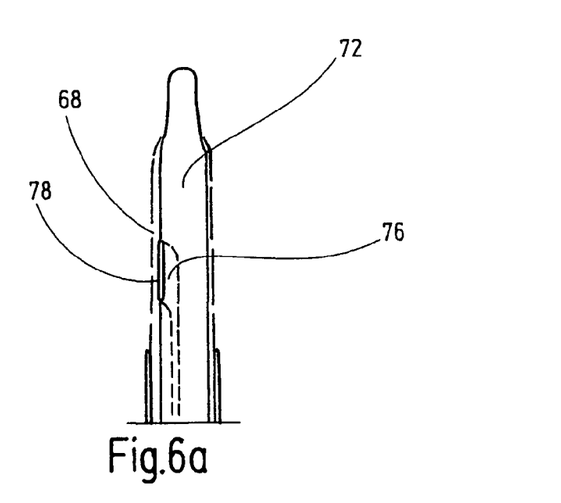
FIG. 6a shows the distal end of another embodiment of the device, which has a membrane-like cover on the passage.
Figure 6B:
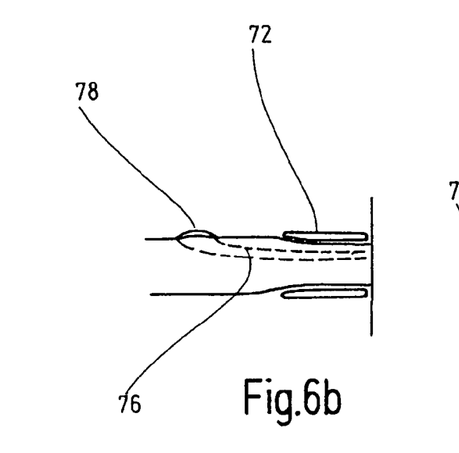
FIG. 6b shows the membrane-like cover of the embodiment from FIG. 5a for the outlet at the proximal end of the device or passage.

FIGS. 6a and 6b show details of another embodiment of the device according to the invention. In FIGS. 6a and 6b, the same reference numbers as in FIG. 5 have been used where identical elements are being described. It will be seen from FIGS. 6a and 6b that the passage 76 is covered with a membrane-like cover 78 at its inlet (see FIG. 6b) in the distal area of the dilator 72 and at its outlet (see FIG. 6a). In this embodiment, the passage is filled with a medium, for example saline solution. When the cannula is inserted into a vessel, the membrane is pressed in as soon as it comes into contact with the flow of blood. By transfer of pressure to the medium present in the passage 76, the membrane at the outlet bulges out, as a result of which the user can again tell that the cannula has reached the vessel.

The invention claimed is:

1. Device for cannulation of a hollow organ in a mammalian body comprising a cannula that has a proximal end, a distal end, and a central section located between the proximal end and distal end, and the cannula, after introduction into the vessel, being in fluid communication with the vessel, and the distal end having an expandable structure made of a material which can be converted from a non-expanded state to an expanded state, and the expandable structure comprising openings in the material of the expandable structure in the expanded state, wherein said openings in the expanded state permit physiologically sufficient blood flow through the openings in the material outside of the cannula and past the entire distal end of the cannula to an area of the mammalian body located downstream of a cannulation site, wherein the cannula has a wire-reinforced, stent-like main frame, the proximal end and the central section being coated with a plastic in order to form a liquid-tight tube section.

2. Device according to claim 1, wherein the expandable structure is a self-expanding structure.

3. Device according to claim 1, wherein the expandable structure has a material chosen from the group comprising elastic plastics, superelastic plastics, elastic metals, superelastic metals.

4. Device according to claim 1, wherein the expandable structure has a material with shape-memory properties.

5. Device according to claim 4, wherein the material is nitinol.

6. Device according to claim 1, wherein the expandable structure has the configuration of a self-expandable braided stent.

7. Device according to claim 6, wherein the braided stent or the stent-like main frame has variable angles along its length.

8. Device for cannulation of a hollow organ in a mammalian body comprising a cannula that has a proximal end, a distal end, and a central section located between the proximal end and distal end, and the cannula, after introduction into the vessel, being in fluid communication with the vessel, and the distal end having an expandable structure made of a material which can be converted from a non-expanded state to an expanded state, and the expandable structure comprising openings in the material of the expandable structure in the expanded state, and the device comprising a dilator with a proximal area and a distal area and with a central section located between the proximal area and distal area, which dilator is used to insert the cannula and is provided inside the latter, wherein said openings permit physiologically sufficient blood flow through the openings in the material outside of the cannula and past the entire distal end of the cannula to an area of the mammalian body located downstream of a cannulation site.

9. Device according to claim 8, wherein the expandable structure can be displaced along its length through the dilator.

10. Device according to claim 8, wherein the dilator has a channel-like passage that extends from the distal area of the dilator to at least the central section of the dilator.

11. Device for cannulation of a hollow organ in a mammalian body comprising a cannula that has a proximal end, a distal end, and a central section located between the proximal end and distal end, and the cannula, after introduction into the vessel, being in fluid communication with the vessel, and the distal end having an expandable structure which can be converted from a non-expanded state to an expanded state, and the expandable structure comprising openings in the material of the expandable structure in the expanded state, and the device comprising a dilator with a proximal area and a distal area and with a central section located between the proximal area and distal area, which dilator is used to insert the cannula and is provided inside the latter, the device having a channel-like passage that extends from the distal area of the dilator to at least the central section of the dilator, wherein the channel-like passage is provided as an elongate depression on the surface of the dilator, one end of the passage being provided as an inlet in the distal area of the dilator, and the other end of the passage being provided as an outlet in the proximal end or in the central section, wherein said openings permit physiologically sufficient blood flow through the openings in the material outside of the cannula and past the entire distal end of the cannula to an area of the mammalian body located downstream of a cannulation site.

12. Device according to claim 11, wherein the inlet and the outlet are each provided with a membrane-like cover.

13. Device according to claim 11, wherein the passage contains a free-flowing or gaseous medium.

14. Device according to claim 1, wherein the cannula has variable diameters along its length.

15. Device according to claim 8, wherein the cannula has variable diameters along its length.

16. Device according to claim 11, wherein the cannula has variable diameters along its length.

\* \* \* \* \*